US010792594B2

(12) United States Patent
Pavlik

(10) Patent No.: US 10,792,594 B2
(45) Date of Patent: Oct. 6, 2020

(54) DUAL PUMPING ARRANGEMENT FOR A HOLLOW FIBER FILTER

(71) Applicant: REPLIGEN CORPORATION, Waltham, MA (US)

(72) Inventor: Rudolf Pavlik, Waltham, MA (US)

(73) Assignee: Replegin Corporation, Waltham, MA (US)

( * ) Notice: Subject to any disclaimer, the term of this patent is extended or adjusted under 35 U.S.C. 154(b) by 349 days.

(21) Appl. No.: 15/856,204

(22) Filed: Dec. 28, 2017

(65) Prior Publication Data

US 2019/0201819 A1    Jul. 4, 2019

(51) Int. Cl.
*B01D 29/90* (2006.01)
*B01D 35/26* (2006.01)
(Continued)

(52) U.S. Cl.
CPC ............ *B01D 29/908* (2013.01); *B01D 29/11* (2013.01); *B01D 35/26* (2013.01); *B01D 37/04* (2013.01);
(Continued)

(58) Field of Classification Search
CPC ...... B01D 29/908; B01D 29/11; B01D 35/26; B01D 37/04; B01D 69/08; B01D 29/88; B01D 29/92; B01D 61/10; B01D 61/12; B01D 61/20; B01D 61/22; B01D 63/02; B01D 63/06; B01D 65/00; B01D 65/08; B01D 2201/20; B01D 2201/202; B01D 2201/54; B01D 2221/10; B01D 2311/06; B01D 2311/14; B01D 2311/16; B01D 2313/24; B01D 2313/243; B01D 2315/10; B01D 2317/04; B01D 2321/205; B01D 2321/2083; C12M 29/10; C12M 25/02; C12M 1/126; C12M 29/16; C12M 33/14; C12M 41/48; C12M 47/12; F04B 9/00; F04B 9/02; F04B 9/08; F04B 9/10; F04B 9/103; F04B 9/109; F04B 9/12;
(Continued)

(56) References Cited

U.S. PATENT DOCUMENTS 1,994,460 A * 3/1935 Bijur ........................ F16N 7/385
 184/7.3
2,145,854 A * 2/1939 Bijur ........................ B60R 17/02
 184/29

(Continued)

FOREIGN PATENT DOCUMENTS

WO    WO2013106458 A2    7/2013

OTHER PUBLICATIONS

International Search Report and Written Opinion dated Mar. 1, 2019 for PCT/US 2018/067112 filed Dec. 21, 2018.

*Primary Examiner* — Joseph W Drodge

(57) ABSTRACT

A fluid filtration assembly includes a filter housing having first and second ends and a connector for fluid communication with a fluid storage vessel. A filter element is disposable within the filter housing, and first and second pumps are coupled at the first and second ends of the filter housing. A controller may coordinate the operation of the first and second pumps to induce alternating tangential flow of fluid between the filter housing and the first and second pumps. At least one of the first and second pumps is a diaphragm pump or a plunger pump. The fluid storage vessel can be a bioreactor.

22 Claims, 7 Drawing Sheets

(51) Int. Cl.
*B01D 29/11* (2006.01)
*C12M 1/36* (2006.01)
*C12M 1/00* (2006.01)
*B01D 37/04* (2006.01)
*B01D 63/00* (2006.01)

(52) U.S. Cl.
CPC ............ *B01D 63/00* (2013.01); *C12M 29/00* (2013.01); *C12M 29/04* (2013.01); *C12M 29/16* (2013.01); *C12M 41/48* (2013.01); *C12M 47/10* (2013.01)

(58) Field of Classification Search
CPC ........ F04B 9/1207; F04B 9/129; F04B 9/135; F04B 9/137; F04B 19/02; F04B 19/022; F04B 23/04; F04B 23/06; F04B 23/08; F04B 23/103; F04B 23/106; F04B 23/1214; F04B 43/02; F04B 43/06; F04B 43/0054; F04B 43/0063; F04B 43/0072; F04B 43/0081; F04B 43/009; F04B 43/04; F04B 43/09; F04B 43/086; F04B 45/04; F04B 45/047; F04B 45/053; F04B 45/065; F04B 45/067; F04B 45/073; F04B 49/00; F04B 49/10; F04B 49/12; F04B 49/20; F04B 53/20; F04B 2201/02; F04B 2201/0201; F04B 2201/0202; F04B 2201/0206; F04B 2201/0207; F04B 2205/00; F04B 2205/01; F04B 2205/03
USPC ...... 210/141, 143, 257.1, 257.2, 258, 321.6, 210/321.78, 321.79, 321.8, 321.87, 210/321.88, 321.89, 340, 416.1, 456; 417/1, 2, 3, 62, 92, 93, 95–98, 103, 212, 417/274, 313; 435/297.1, 297.4, 308.1
See application file for complete search history.

(56) References Cited

U.S. PATENT DOCUMENTS

| | | | | |
|---|---|---|---|---|
| 2,923,375 | A * | 2/1960 | White | F24F 3/1603 96/240 |
| 3,269,541 | A * | 8/1966 | Neely | B01D 35/147 210/132 |
| 4,735,726 | A * | 4/1988 | Duggins | A61M 1/3496 210/321.75 |
| 4,897,189 | A * | 1/1990 | Greenwood | A61M 1/30 210/195.2 |
| 7,291,267 | B2 * | 11/2007 | Johnson | B01D 17/0202 210/321.69 |
| 9,446,354 | B2 * | 9/2016 | Shevitz | C12M 29/16 |
| 10,166,497 | B1 * | 1/2019 | Pavlik | F04B 43/0081 |
| 2005/0167346 | A1 * | 8/2005 | Johnson | B01D 17/0202 210/106 |
| 2007/0158256 | A1 | 7/2007 | Kromkamp et al. | |
| 2011/0223581 | A1 | 9/2011 | Stobbe | |
| 2013/0059371 | A1 * | 3/2013 | Shevitz | C12M 29/16 435/297.4 |
| 2013/0270165 | A1 | 10/2013 | Shevitz | |
| 2015/0037831 | A1 * | 2/2015 | Lee | C12M 47/02 435/29 |
| 2015/0164690 | A1 | 6/2015 | Peterson | |
| 2015/0247114 | A1 | 9/2015 | Gebauer | |
| 2016/0030888 | A1 * | 2/2016 | Diemer | B01D 63/081 210/321.84 |
| 2017/0157579 | A1 * | 6/2017 | Vogt | B01F 7/16 |
| 2017/0232390 | A1 * | 8/2017 | Matsuzaki | B01D 61/32 424/450 |

* cited by examiner

DUAL PUMPING ARRANGEMENT FOR A HOLLOW FIBER FILTER

BACKGROUND OF THE DISCLOSURE

Field of the Disclosure

Embodiments of the disclosure relate generally to filtration systems, and more particularly to an alternating tangential flow filtration unit that includes a housing and first and second pumps for alternating flow through a filter element disposed in the housing.

Discussion of Related Art

Filtration is typically performed to separate, clarify, modify, and/or concentrate a fluid solution, mixture, or suspension. In the biotechnology, pharmaceutical, and medical industries, filtration is vital for the successful production, processing, and analysis of drugs, diagnostics, and chemicals as well as many other products. As examples, filtration may be used to sterilize fluids and to clarify a complex suspension into a filtered "clear" fraction and an unfiltered fraction. Similarly, constituents in a suspension may be concentrated by removing or "filtering out" the suspending medium. Further, with appropriate selection of filter material, filter pore size and/or other filter variables, many other specialized uses have been developed. These uses may involve selective isolation of constituents from various sources, including cultures of microorganisms, blood, as well as other fluids that may be solutions, mixtures, or suspensions.

Biologics manufacturing processes have advanced through substantial process intensification. Both eukaryotic and microbial cell culture to produce recombinant proteins, virus-like particles (VLP), gene therapy particles, and vaccines now include cell growth techniques that can achieve 100e6 cells/ml or higher. This is achieved using cell retention devices that remove metabolic waste products and refresh the culture with additional nutrients. One of the most common means of cell retention is to perfuse a bioreactor culture using hollow fiber filtration using alternating tangential flow (ATF). Commercial and development scale processes use a device that controls a pump to perform ATF through a hollow fiber filter.

As shown in FIG. 1, a hollow fiber filter module 1 is vertically oriented, with a diaphragm pump 2 conventionally located on the bottom end 4 of the hollow fiber filter module. An inlet and return 6 from and to a vessel, such as a bioreactor vessel (not shown), is positioned on a side of the filter module 1 opposite the pump 2. The hollow fiber filter 8 is thus positioned between the vessel and the pump 2. As will be appreciated, the hollow fiber filter 8 represents a restriction in the flow of liquid between the pump 2 and the vessel, and as a result, the hollow fiber filter is not uniformly utilized along its entire length.

In addition, the use of a single diaphragm pump in such an arrangement has inherent limitations because it uses a vacuum on the underside of the diaphragm during the "pull" cycle in order to draw liquid from the process vessel down through the filter. The maximum "vacuum" that can be applied, however, is about −14.5 psi. This vacuum can be further impacted by losses in the tubing/piping and components between the vacuum source and the diaphragm pump. In addition, if the viscosity of the fluid changes, there may be a requirement for more negative pressure behind the diaphragm to obtain a full displacement of the pump. All of these factors can reduce the efficiency of conventional pumping systems.

It would be desirable, therefore, to provide an improved pumping arrangement that increases the utilization of the entire filter length of a hollow fiber filter used in connection with a vessel such as a bioreactor vessel. It would also be desirable to provide a pumping arrangement that enhances the overall efficiency of the pumping system.

SUMMARY OF THE DISCLOSURE

A fluid filtration assembly is disclosed, including a filter housing having first and second ends, and a coupling for fluid connection with a fluid storage vessel. A filter element may be disposable within the filter housing. A first pump is coupled at the first end of the filter housing and a second pump is coupled at the second end of the filter housing. The first and second pumps can be configured to move fluid from the fluid storage vessel through the filter element.

In some embodiments, at least one of the first and second pumps is a diaphragm pump or a plunger pump. The filter element can be a hollow fiber filter. The first and second pumps can be controllable to generate alternating tangential flow of the fluid between the filter housing and the first and second pumps. The first and second pumps can be separately controllable. The first and second pumps can be controllable such that a vacuum stroke of the first pump is synchronized with a pressure stroke of the second pump. The first and second pumps can be controllable so that a diaphragm of the first pump applies a positive pressure to the fluid while a diaphragm of the second pump is under negative pressure.

A fluid filtration assembly is disclosed, including a process vessel, a filter housing having first and second ends, and a coupling for fluid communication with the process vessel. A filter element can be disposed within the filter housing. A first pump is coupled at the first end of the filter housing and a second pump is coupled at the second end of the filter housing. The first and second pumps can be configured to move fluid from the fluid storage vessel through the filter element.

At least one of the first and second pumps can be a diaphragm pump or a plunger pump. The filter element can be a hollow fiber filter. The first and second pumps can be controllable to generate alternating tangential flow of the fluid between the filter housing and the first and second pumps. The system can include a controller including a processor programmed to execute instructions to control the first and second pumps. The processor may be programmed to execute instructions to control the first and second pumps so that a vacuum stroke of the first pump is synchronized with a pressure stroke of the second pump. The processor may be programmed to execute instructions to control the first and second pumps so that a diaphragm of the first pump applies a positive pressure to the fluid while a diaphragm of the second pump is under negative pressure.

A fluid filtration assembly is disclosed, and includes a process vessel, a filter housing having first and second ends, and a coupling for fluid communication with the process vessel. A filter element is disposable within the filter housing. A first pump is coupled at the first end of the filter housing and a second pump coupled at the second end of the filter housing. The first and second pumps can be configured to move fluid from the fluid storage vessel through the filter element. A controller can be in communication with the first and second pumps for simultaneously actuating the first and second pumps to cycle fluid between the first and second pumps and the process vessel.

At least one of the first and second pumps is a diaphragm pump or a plunger pump. The controller comprises a processor programmed to execute instructions to control operation of the first and second pumps. The processor may be programmed to execute instructions to control the first and second pumps to generate alternating tangential flow of the fluid between the filter housing and the first and second pumps. The processor may be programmed to execute instructions to control the first and second pumps so that a vacuum stroke of the first pump is synchronized with a pressure stroke of the second pump. The processor may be programmed to execute instructions to control the first and second pumps so that a diaphragm of the first pump applies a positive pressure to the fluid while a diaphragm of the second pump is under negative pressure.

BRIEF DESCRIPTION OF THE DRAWINGS

The accompanying drawings illustrate preferred embodiments of the disclosed method so far devised for the practical application of the principles thereof, and in which.

DESCRIPTION OF EMBODIMENTS

A pump and filter assembly is disclosed, comprising a filter housing containing a filter, and first and second pumps which move fluid in alternating directions through the filter. In some embodiments, the filter housing is connected to a vessel, such as a bioreactor vessel, for filtering the contents thereof. The assembly can be employed for conducting a rapid, low sheer, Alternating Tangential Flow (ATF) of fluid through the filter, which in some embodiments is a hollow fiber filter. Such a system has applications in perfusion of cultured animal cells as well as other varied filtration applications.

As will be discussed in greater detail later, the disclosed assembly can provide a more uniform use of the filter as compared to current systems. By employing two pumps positioned at opposite ends of the filter, and by synchronizing the action of both pumps, a more robust pumping action and more uniform filter utilization can be achieved compared to current systems that use only a single pump. In some embodiments, the two pumps are independently controlled, which can provide an additional degree of flow controllability. Further, operational control of the two pumps can be based on an algorithm which can periodically apply an operational subroutine that facilitates a filter cleaning/backflush function. These and other advantage will be discussed below.

Figure 1:
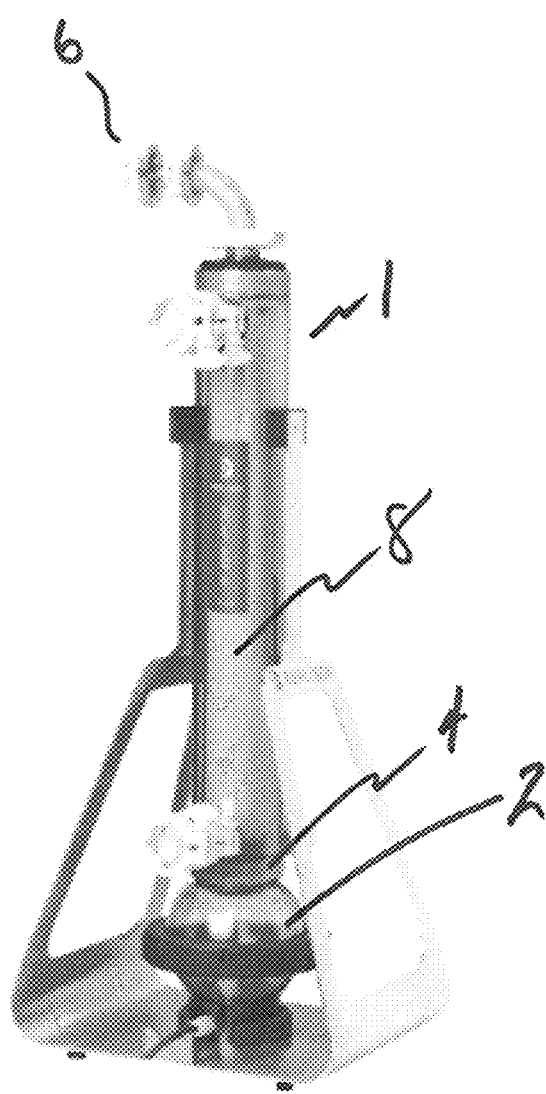
FIG. 1 is an isometric view of a conventional filter module and diaphragm pump arrangement.
Figure 2:
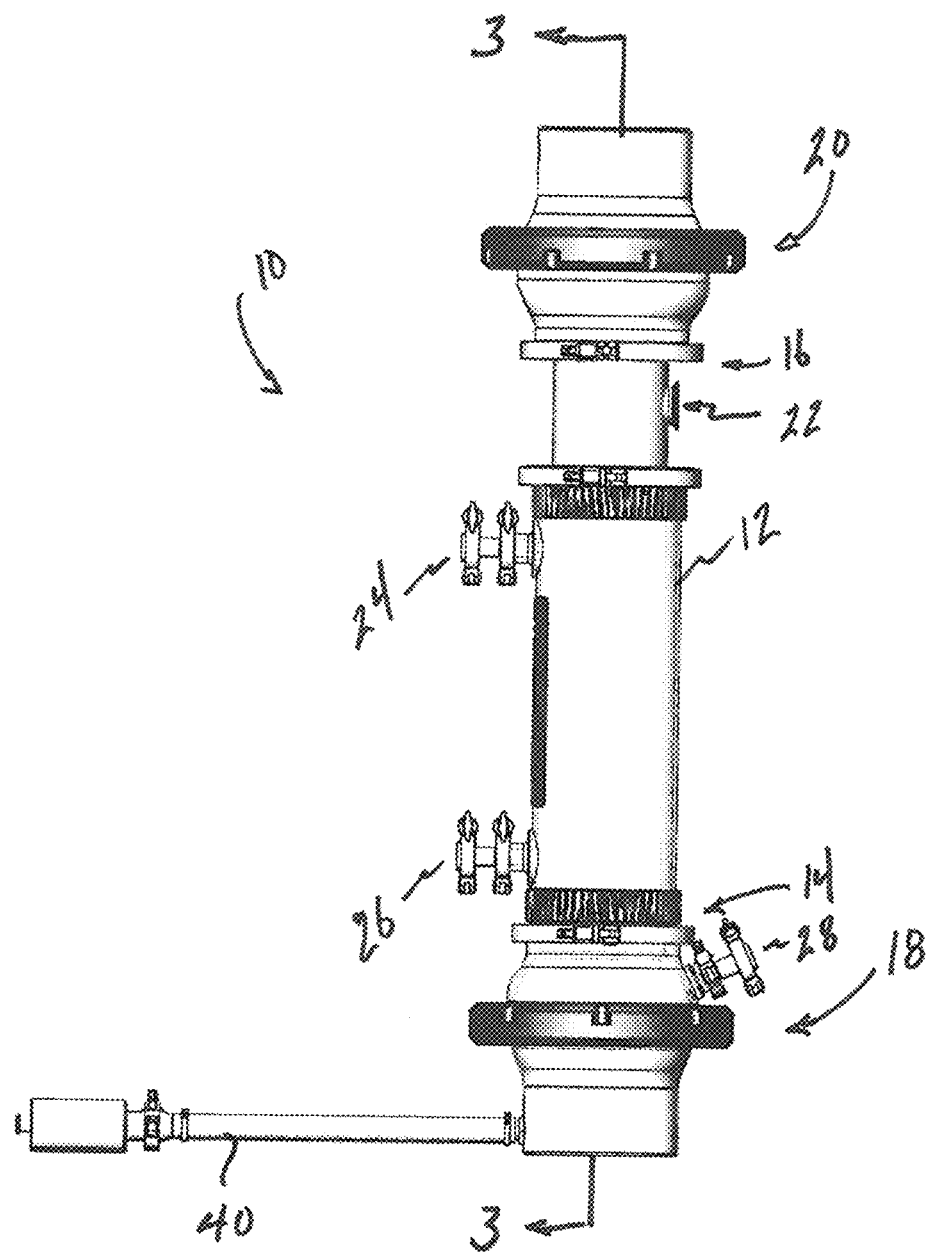
FIG. 2 is a side view of an example pump and filter assembly according to the present disclosure.
Figure 3:
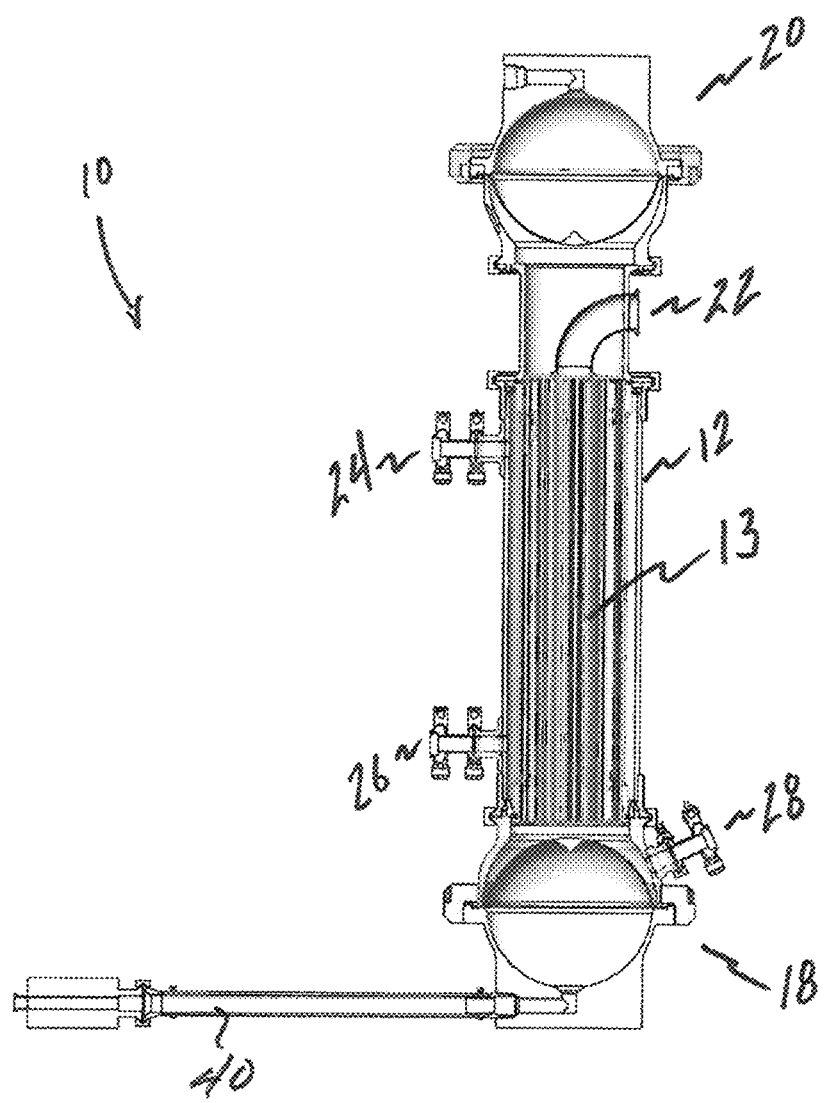
FIG. 3 is a cross-section view of the pump and filter assembly of FIG. 2 taken along line 3-3 of FIG. 2.

FIGS. 2 and 3 illustrate an example pump and filter assembly 10, which can include a filter housing 12 having first and second ends 14, 16. The filter housing 12 encloses a filter element 13, which in one non-limiting exemplary embodiment, is a hollow fiber filter. A first pump 18 is coupled to the first end 14 of the filter housing 12 and a second pump 20 is coupled the second end 16 of the filter housing. In the illustrated embodiment the first and second pumps 18, 20 are diaphragm pumps, but it will be appreciated that the disclosure is not so limited, and thus the first and second pumps can be any appropriate pump type, including plunger pumps and the like. In addition, the first and second pumps 18, 20 may be different pump types, and/or may be of different sizes, capacities, etc. In some embodiments, the pump and filter assembly 10 is a single use integral assembly for filtering fluid stored in a process vessel (not shown).

The pump and filter assembly 10 can include a fluid connection port 22 disposed in the filter housing 12 for coupling the pump and filter assembly to a process vessel to receive fluid from the vessel and to provide filtered fluid back to the vessel. The pump and filter assembly 10 can also include a plurality of ports, such as a fluid harvest port 24 for removing filtered fluid from the filter housing, a fluid monitoring port 26 for coupling a pressure valve or transducer, and a fluid sample port 28 for coupling a sampler valve. As will be appreciated, a sampler valve may be used for sampling the quality of the fluid in the first pump 18, injecting or expelling liquid or gas into and out of the pump, and injecting sterilizing steam into the system and/or removing resulting steam condensate from the system.

Although not shown, the process vessel may be any suitable container for housing a fluid to be filtered. For example, it may be a bioreactor, a fermentor or any other vessel, nonexclusively including vats, barrels, tanks, bottles, flasks, containers, and the like which can contain liquids. The process vessel may be composed of any suitable material such as plastic, metal such as stainless steel, glass, or the like. Appropriate fluid connectors (piping, tubing, couplings, valves) can be used to fluidly couple the process vessel to the pump and filter assembly 10.

The filter housing 12 can be made from plastic, metal, such as stainless steel, glass, and the like. Suitable filter elements 13 include hollow fiber filters, screen filters, and the like. In one non-limiting example embodiment, the filter element 13 is a hollow fiber filter. According to the disclosure, pump and filter assembly 10 can be configured for single use (i.e., disposable), with the filter housing 12, filter element 13 and first and second pumps 18, 20 provided together as an integral assembly. Alternatively, in some embodiments only the filter housing 12 and filter element 13 may be configured for single use, and may be removably connectable to the first and second pumps 18, 20, one or both of which may be reusable.

Various advantages exist in providing the pump and filter assembly 10 as a single-use (disposable) assembly. For example, the assembly can be set up with minimal handling and do not require cleaning or sterilization by the user, since the components are supplied sterile and in a form ready to use with minimal preparation and assembly. This can result in cost savings due to reduced labor and handling by the user along with elimination of a long autoclave cycle. Furthermore, at the end of their use, the assembly can be readily discarded without cleaning. A disposable assembly reduces risk of contamination and assembly by operators, and do not require lengthy validation procedures for operation/sterilization. The components of the assembly also can be lighter and easier to transport, and are less expensive and take up less storage space compared to stainless steel or glass units.

Figure 4:
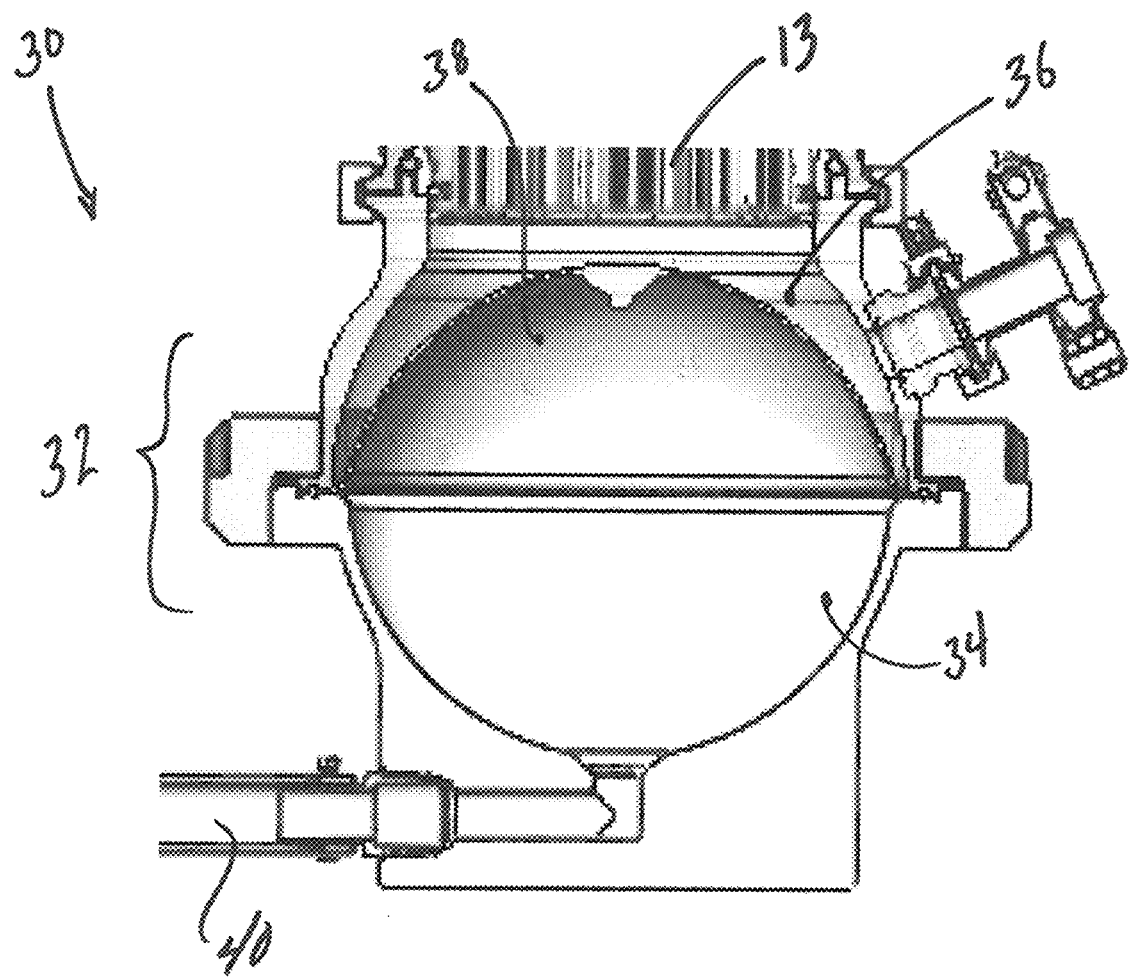
FIGS. 4 and 5 are cross-section views of example diaphragm pumps for use with the pump and filter assembly of FIG. 2.

FIG. 4 shows an exemplary diaphragm pump 30 for use as the first pump 18 illustrated in FIGS. 2 and 3. In general, the diaphragm pump 30 includes a pump housing 32 separated into first and second interior chambers 34, 36 by an internal flexible diaphragm 38. The pump 30 is actuated by feeding compressed air into the first chamber 34 of the pump via a gas inlet 40, filling the first chamber with the gas, and forcing the diaphragm 38 to expand the first chamber and to move fluid in the second chamber 36 so that it passes through the filter element 13 and into (via fluid connection port 22) an attached process vessel, such as a bioreactor vessel. When the gas is drawn back through the gas inlet 40, such as by a vacuum source, the diaphragm 38 is drawn towards the gas inlet, which causes the first chamber 34 to decrease in volume, and draws flow from the process vessel (via fluid connection port 22) through the filter element 13 and into the expanding second chamber 36. This action can be repeated, drawing fluid back and forth from the process vessel, through the filter element 13, and second chamber 36, thereby causing an alternating flow tangentially through the filter.

Figure 5:
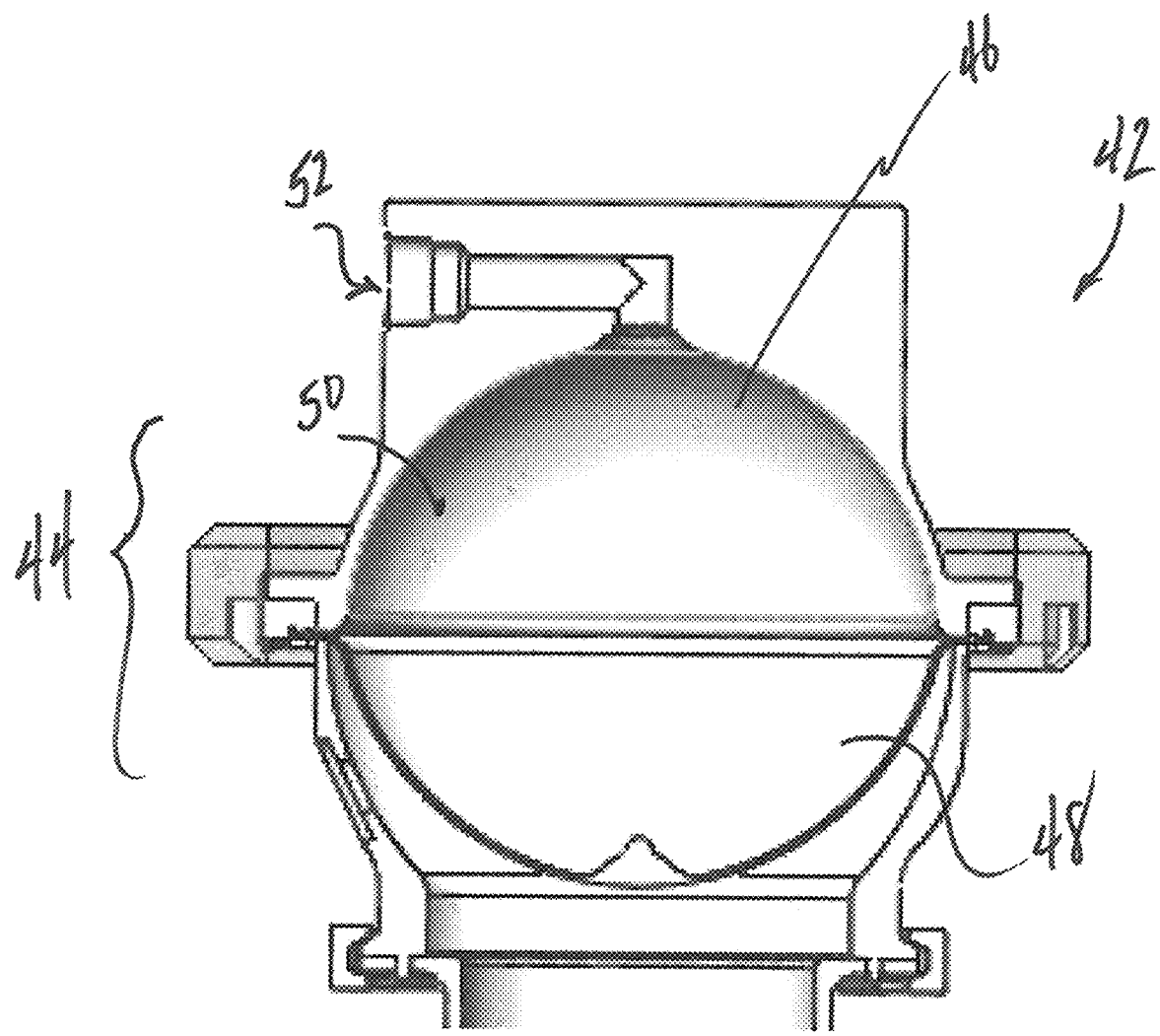

FIG. 5 shows an exemplary diaphragm pump 42 for use as the second pump 20 illustrated in FIGS. 2 and 3. In general, the diaphragm pump 42 is similar in form and function to the diaphragm pump 30 shown in FIG. 4. Thus, the diaphragm pump 42 includes a pump housing 44 separated into first and second interior chambers 46, 48 by an internal flexible diaphragm 50. The pump 42 is actuated by feeding compressed air into the first chamber 46 of the pump via a gas inlet 52, filling the first chamber with the gas, and forcing the diaphragm 50 to expand the first chamber and to move fluid in the second chamber 36 so that it passes downward through the filter element 13. When the gas is drawn back through the gas inlet 52, such as by a vacuum source, the diaphragm 50 is drawn towards the gas inlet, which causes the first chamber 46 to decrease in volume, and draws upward through the filter element 13 toward the expanding second chamber 48. This action can be repeated, drawing fluid back and forth from the process vessel, through the filter element 13, and second chamber 48, thereby causing an alternating flow tangentially through the filter element.

With the disclosed arrangement, pumping can consist of two cycles, a pressure cycle and a vacuum cycle. The vacuum cycle under the diaphragm 38 (referred to as the air side) pulls liquid from the process vessel through the filter element 13, while the pressure cycle under the diaphragm 38 pushes the liquid through the filter into the process vessel. The liquid is filtered, and a portion is evacuated as a filtrate from the fluid harvest port 24, while a portion of volume of liquid, during the pressure part of the cycle, is returned to the process vessel through fluid connection port 22. The volume difference between the liquid returned to the process vessel and the volume of filtrate collected via the fluid harvest port 24 is constant, and is dependent on the size of the hollow fiber filter element 13, as well as process requirements.

In some embodiments, the first and second pumps 18, 20 can be proportionally sized (e.g., the first pump would have a different displacement volume than the second pump, or the first pump would have a different stroke than the second pump) to reflect a desired flow distribution between the process vessel and filtrate collection. For example, the upper and lower pump volume difference can be used to provide desired liquid exchanges between the process vessel and the filter element 13, as well as desired filtrate collection volumes. As will be understood, to reduce the chance for cell damage residence time of a cell culture outside of the process vessel (i.e., in the region of the filter element 13 and first and second pumps 18, 20) should be minimized. By implementing a volume difference between the first and second pumps 18, 20, the liquid exchanges temporarily contained in the filter and pump can be controlled and enhanced.

As previously noted, the disclosed arrangement provides increased robustness in pumping when operation of the first and second pumps 18, 20 are synchronized. For example, it will be appreciated that in some embodiments the vacuum stroke of the first pump 18 can be synchronized with the positive pressure stroke of the second pump 20, and vice versa. That is, as the diaphragm of one pump applies positive pressure to the fluid, the diaphragm of the other pump is under negative (i.e., vacuum) pressure. Such complimentary operation of the first and second pumps 18, 20 can enhance overall effectiveness of pumping of the process liquid through the filter element 13, since the vacuum stroke of each pump will be enhanced by the positive pressure stroke of the opposite pump.

The benefit of such an arrangement is that positive pressure is limited only by the characteristics of the pump, and thus the positive pressure stroke of the pumps 18, 20 provides the more robust portion of the cycle. Negative pressure availability is naturally limited, and thus the negative pressure stroke of the pumps 18, 20 is the weaker part of the cycle. By providing liquid movement assist via one pump in the positive pressure mode, while the other pump is in the negative pressure mode, makes the overall pumping action stable and uniform.

In some embodiments, the negative pressure stroke(s) may be eliminated entirely from the overall pumping cycle. In such arrangements, alternating positive pressure strokes between the first and second pumps 18, 20 may be used to move fluid back and forth with respect to the filter element 13. For example, when positive pressure is applied to one of the pumps 18, 20, the opposite pump 20, 18 may be allowed to move freely (i.e., the associated diaphragm 38, 50 is simply allowed to be moved by the motion of the fluid). On the end of each positive pressure stroke, the "free" moved pump takes over, and under positive pressure moves the liquid while the opposite pump is allowed to move freely. Such an arrangement would eliminate the need for a vacuum source to be applied to the first and second pumps 18, 20, thus simplifying the overall system.

In some embodiments, the first and second pumps 18, 20 are controlled independently, providing additional variability in the control of fluid through the filter element 13. This control can be either manual or automated. Thus, operation of the first and second pumps 18, 20 can be controlled by an algorithm, which can be selectable by a user, or may in some cases be automatically selected based on the type and size of filter element 13, the type of fluid being filtered, and the like.

As will be described in greater detail later, in some embodiments, actuation of the first and second pumps 18, 20 will be controlled by controller 76 including a microprocessor or programmable logic circuit (PLC) which allows the system to operate the pumps in a variety of sequences and manners. For example, the processor of the controller 76 could execute instructions (e.g., a subroutine) to apply a temporary difference in stroke sequence between the first and second pumps 18, 20. Such operation may offer beneficial benefits to the process or longevity of the filter. As will be appreciated, the controller 76 may apply any of a variety of adjustments to pump operation, which can be stored in controller memory and executed by the controller processor upon user command or automatically.

Figure 6:
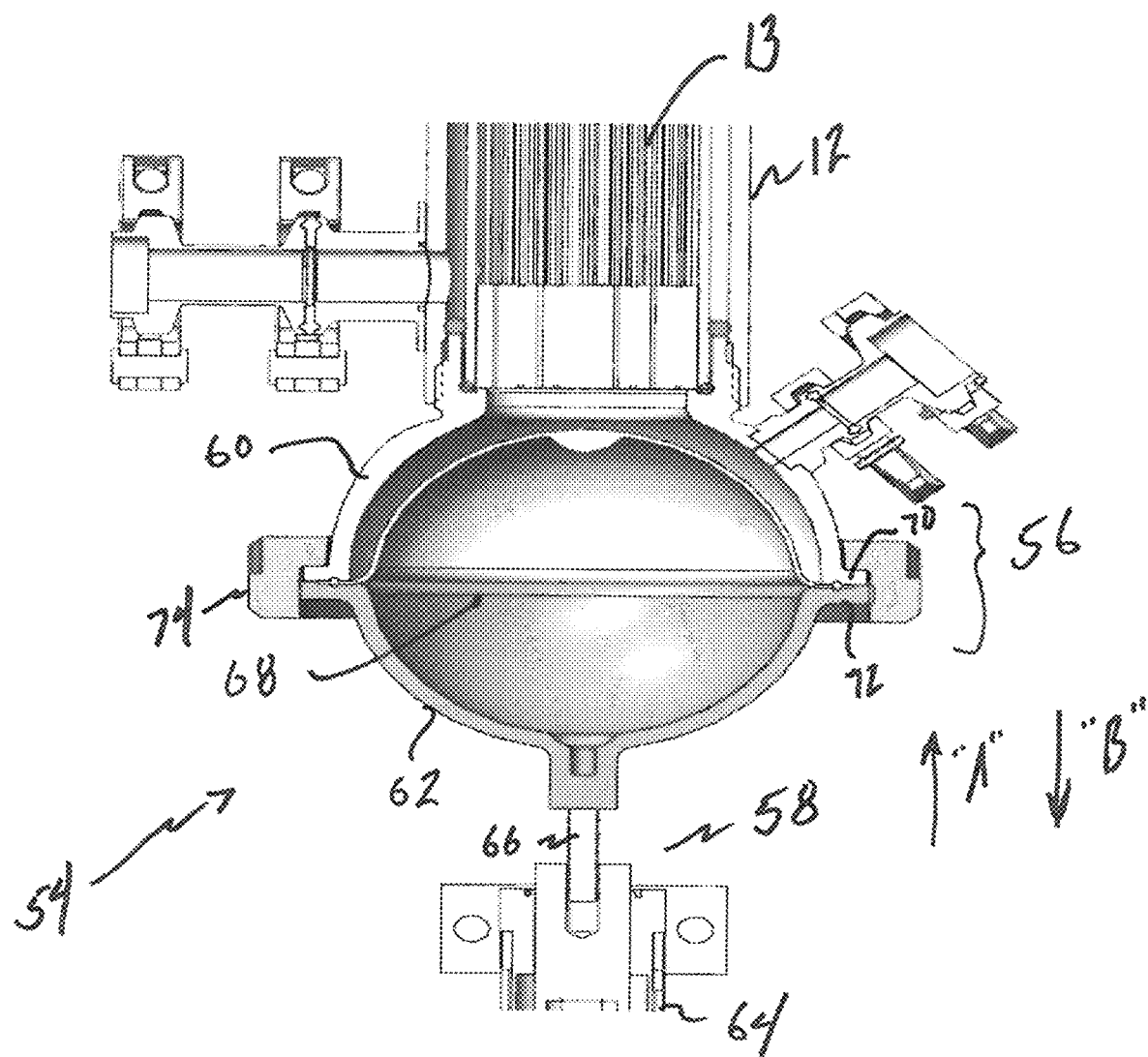
FIG. 6 is a cross-section view of an example plunger pump for use with the pump and filter assembly of FIG. 2.

As previously noted, one or both of the first and second pumps 18, 20 may be of a type other than a diaphragm pump. FIG. 6 shows an exemplary plunger pump 54 for use as the first and/or second pump 18, 20 illustrated in FIGS. 2 and 3. The plunger pump 54 can include a housing portion 56 and an actuator portion 58. The housing portion 56 may include a rigid portion 60 and a flexible portion 62 coupled together. The flexible portion 62 may also be coupled to the actuator portion 58 so that the flexible portion 62 is movable with respect to the rigid portion 60 in response to activation of the actuator portion. The actuator portion 58 may include a cylinder housing 64, and a driven rod portion 66 that is selectively movable within the cylinder housing. A servo motor, cam, pneumatic or electrical actuator can be used to selectively move the rod portion 66 in the directions of arrows "A" and "B" to cause the plunger pump 54 to move fluid through the filter element 13 in manner similar to that described in relation to the diaphragm pump 30 illustrated in FIG. 4.

As best seen, the rigid portion 60 and flexible portion 62 of the housing 56 can each be bell-shaped members that can be coupled together to provide the housing portion with a globe shape having an interior volume 68 defined by respective inner surfaces of the rigid and flexible portions. The rigid portion 60 and flexible portion 62 have respective radially extending flanges 70, 72 that can contact each other and can be clamped together via clamp or nut 74. Alternatively, the flexible portion 62 can be formed from an elastomer that is overmolded on the rigid portion 60, thus eliminating the need for a clamp 74.

As will be appreciated, expansion or contraction of the flexible portion 62 can generate vacuum and pressure required to initiate movement of fluid between the first pump 18 and the process vessel. Where the second pump 20 is a plunger pump similar to that described in relation to FIG. 6, operation of the first and second pumps 18, 20 can be synchronized in a similar fashion to that previously described, such that the first and second pumps complement each other. For example, the "vacuum" stroke of each pump will be enhanced by the "pressure" stroke of the opposite pump when the pumps 18, 20 are synchronized (i.e., one flexible portion 62 applies pressure when the other pump is at vacuum.)

Figure 7:
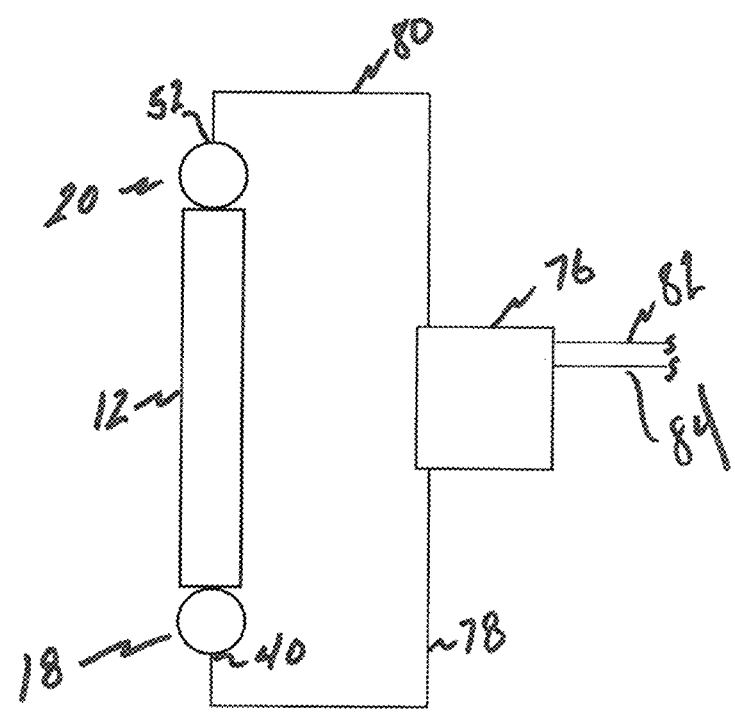
FIG. 7 is a schematic of an example control system for use with the pump and filter assembly of FIG. 2.

In some embodiments, operation of the first and second pumps 18, 20 can be automated via a controller. FIG. 7 shows a controller 76 coupled to the first and second pumps 18, 20 via first and second gas inlet/exhaust lines 78, 80, for controlling the movement of the diaphragms 38, 50 within the first and second pumps. The controller 76 may include gas supply and exhaust lines 82, 84 connected to gas service infrastructure of a building or the like. By controlling the pressure applied behind the diaphragms 38, 50, the controller 76 can control the flow of fluid flow back and forth through the filter element 13 according to a desired set of cycle parameters.

As previously mentioned, the controller 76 can include a processor and associated memory for storing information regarding the first and second pumps 18, 20, the filter element 13 and/or other aspects of the system. The memory can include instructions executable by the processor for controlling operation of the first and second pumps 18, 20 to thereby control flow of fluid back and forth through the filter element 13 in any of a variety of desired manners. The controller 76 can also include a user interface for allowing a user to input information into the controller and/or operate the controller and the associated first and second pumps 18, 20 in a desired manner.

Although in the illustrated embodiment the controller 76 is shown as being coupled to the first and second pumps 18, 20 via first and second gas inlet/exhaust lines 78, 80, it will be appreciated that when the first and second pumps are not diaphragm pumps, other connection types can be used. For example, where one or both of the first and second pumps 18, 20 is a plunger pump (FIG. 6), the controller 76 may be coupled to the actuator portion(s) 58 via a hard-wired or wireless connection to control the pump(s) in a desired manner to control flow of fluid back and forth through the filter element 13.

In use, the first and second pumps 18, 20 can generate an alternating tangential flow through the filter element 13. The first and second pumps 18, 20 can generate a reversible flow of liquid such as a culture suspension, back and forth, between the process vessel and the first pump 18. For example, flow from the housing 12 through the filter element 13 to the process vessel is generated by applying positive pressure beneath the diaphragm 38 of the first pump 18, and by applying vacuum pressure above the diaphragm 50 of the second pump 20. Movement of diaphragm 38 of the first pump 18 expels liquid from the housing 32 of the first pump, moving the liquid towards the process vessel, and generating a tangential flow in one direction. Final, filtered product is removed through harvest port 24 by, for example, a peristaltic pump. In the reverse, flow from the process vessel through the filter element 13 and housing 12 is generated by applying positive pressure above the diaphragm 50 of the second pump 20, and by applying negative pressure beneath the diaphragm 38 of the first pump 18. Final, filtered product is removed through harvest port 24 by, for example, a peristaltic pump. Flow from pump 24 to the process vessel and return from the process vessel to the pump 24 completes one cycle.

While the present invention has been disclosed with reference to certain embodiments, numerous modifications, alterations and changes to the described embodiments are possible without departing from the spirit and scope of the invention, as defined in the appended claims. Accordingly, it is intended that the present invention not be limited to the described embodiments, but that it has the full scope defined by the language of the following claims, and equivalents thereof.

What is claimed is:

1. A fluid filtration assembly, comprising:
   a filter housing having first and second ends, and fluidly communicating with a fluid storage vessel;
   a filter element disposable within the filter housing; and
   a first pump coupled to the first end of the filter housing and a second pump coupled to the second end of the filter housing, the first and second pumps operable for pumping fluid from the fluid storage vessel through the filter element.

2. The fluid filtration assembly of claim 1, wherein at least one of the first and second pumps is a diaphragm pump.

3. The fluid filtration assembly of claim 1, wherein at least one of the first and second pumps is a plunger pump.

4. The fluid filtration assembly of claim 1, wherein the filter element is a hollow fiber filter.

5. The fluid filtration assembly of claim 4, wherein the first and second pumps are controllable to generate alternating tangential flow of the fluid between the filter housing and the first and second pumps.

6. The fluid filtration assembly of claim 1, wherein the first and second pumps are separately controllable.

7. The fluid filtration assembly of claim 1, wherein the first and second pumps are controllable such that a vacuum stroke of the first pump is synchronized with a pressure stroke of the second pump.

8. The fluid filtration assembly of claim 1, wherein the first and second pumps are controllable so that a diaphragm of the first pump applies a positive pressure to the fluid while a diaphragm of the second pump is under negative pressure.

9. A fluid filtration assembly, comprising:
a process vessel;
a filter housing having first and second ends, and fluidly communicating with the process vessel;
a filter element disposable within the filter housing; and
a first pump coupled to the first end of the filter housing and a second pump coupled to the second end of the filter housing, the first and second pumps operable for pumping fluid from the process vessel through the filter element.

10. The fluid filtration assembly of claim 9, wherein at least one of the first and second pumps is a diaphragm pump.

11. The fluid filtration assembly of claim 9, wherein at least one of the first and second pumps is a plunger pump.

12. The fluid filtration assembly of claim 9, wherein the filter element is a hollow fiber filter.

13. The fluid filtration assembly of claim 12, wherein the first and second pumps are controllable to generate alternating tangential flow of the fluid between the filter housing and the first and second pumps.

14. The fluid filtration assembly of claim 12, further comprising a controller including a processor programmed to execute instructions to control the first and second pumps.

15. The fluid filtration assembly of claim 14, wherein the processor is programmed to execute instructions to control the first and second pumps so that a vacuum stroke of the first pump is synchronized with a pressure stroke of the second pump.

16. The fluid filtration assembly of claim 14, wherein the processor is programmed to execute instructions to control the first and second pumps so that a diaphragm of the first pump applies a positive pressure to the fluid while a diaphragm of the second pump is under negative pressure.

17. A fluid filtration assembly, comprising:
a process vessel;
a filter housing having first and second ends, and fluidly communicating with the process vessel;
a filter element disposable within the filter housing;
a first pump coupled to the first end of the filter housing and a second pump coupled to the second end of the filter housing, the first and second pumps operable for pumping fluid from the process vessel through the filter element; and
a controller in communication with the first and second pumps configured to actuate the first and second pumps to cycle fluid between the first and second pumps and the process vessel.

18. The fluid filtration assembly of claim 17, wherein at least one of the first and second pumps is a diaphragm pump or a plunger pump.

19. The fluid filtration assembly of claim 17, wherein the controller comprises a processor programmed to execute instructions to control operation of the first and second pumps.

20. The fluid filtration assembly of claim 19, wherein the processor is programmed to execute instructions to control the first and second pumps to generate alternating tangential flow of the fluid between the filter housing and the first and second pumps.

21. The fluid filtration assembly of claim 19, wherein the processor is programmed to execute instructions to control the first and second pumps so that a vacuum stroke of the first pump is synchronized with a pressure stroke of the second pump.

22. The fluid filtration assembly of claim 19, wherein the processor is programmed to execute instructions to control the first and second pumps so that a diaphragm of the first pump applies a positive pressure to the fluid while a diaphragm of the second pump is under negative pressure.

* * * * *